(12) United States Patent
Bhairam et al.

(10) Patent No.: US 10,897,915 B2
(45) Date of Patent: *Jan. 26, 2021

(54) METHOD FOR MAKING COFFEE PRODUCTS CONTAINING CANNABIS INGREDIENTS

(71) Applicant: Blacklist Holdings, Inc., Tacoma, WA (US)

(72) Inventors: Christopher Bhairam, Garden City, NY (US); Zachary Bell, Yomitan-son (JP)

(73) Assignee: Blacklist Holdings, Inc., Tacoma, WA (US)

( * ) Notice: Subject to any disclaimer, the term of this patent is extended or adjusted under 35 U.S.C. 154(b) by 2 days.

This patent is subject to a terminal disclaimer.

(21) Appl. No.: 16/566,852

(22) Filed: Sep. 10, 2019

(65) Prior Publication Data

US 2020/0060305 A1 Feb. 27, 2020

Related U.S. Application Data

(60) Continuation-in-part of application No. 15/837,623, filed on Dec. 11, 2017, now Pat. No. 10,405,560, which is a division of application No. 15/397,895, filed on Jan. 4, 2017, now Pat. No. 9,888,703, which is a continuation of application No. 14/819,830, filed on Aug. 6, 2015, now Pat. No. 9,565,865.

(60) Provisional application No. 62/037,827, filed on Aug. 15, 2014.

(51) Int. Cl.
| | |
|---|---|
| *A61K 36/00* | (2006.01) |
| *A23F 5/14* | (2006.01) |
| *A61K 31/00* | (2006.01) |
| *A23F 5/26* | (2006.01) |
| *B01D 11/02* | (2006.01) |
| *A61K 31/352* | (2006.01) |
| *A61K 36/185* | (2006.01) |

(52) U.S. Cl.
CPC .......... *A23F 5/14* (2013.01); *A23F 5/26* (2013.01); *A61K 31/00* (2013.01); *A61K 31/352* (2013.01); *A61K 36/185* (2013.01); *B01D 11/02* (2013.01); *B01D 11/0288* (2013.01); *A61K 2236/00* (2013.01); *A61K 2236/33* (2013.01)

(58) Field of Classification Search
CPC ..................................................... A61K 36/00
USPC ........................................................ 424/725
See application file for complete search history.

(56) References Cited

U.S. PATENT DOCUMENTS

| | | | |
|---|---|---|---|
| 6,630,507 B1 | 10/2003 | Hampson et al. |
| 6,759,072 B1 | 7/2004 | Gutwein et al. |
| 7,438,941 B2 | 10/2008 | Gutwein et al. |
| 8,222,292 B2 | 7/2012 | Goskonda et al. |
| 8,336,186 B2 | 12/2012 | Bloome et al. |
| 8,481,091 B2 | 7/2013 | Ross |
| 8,586,117 B2 | 11/2013 | Vastardis et al. |
| 8,720,320 B1 | 5/2014 | Rivera |
| 2004/0049059 A1 | 3/2004 | Mueller |
| 2012/0095087 A1 | 4/2012 | Hyatt |
| 2015/0352044 A1 | 12/2015 | Benson et al. |
| 2016/0324776 A1 | 11/2016 | Glatzel |

FOREIGN PATENT DOCUMENTS

| | | |
|---|---|---|
| CN | 105343468 | 2/2016 |
| WO | 2016/135621 | 9/2016 |

OTHER PUBLICATIONS

Website link: http://www.potocoffee.coffee/products (1 page).
Website link: http://www.ganjagrindz.com/products--reviews.html (1 page).
Website link: http://www.houseofjane.com/ (1 page).
Website link: http://fairwindscannabis.com/catapult-coffee/ (1 page).
Website link: http://kushcups.com/details/ (1 page).
Website link: http://www.lordandsterling.com/ (1 page).
Website link: http://en.wikipedia.org/wiki/Tea—The article is about the beverage, Tea (27 pages).

*Primary Examiner* — Michael V Meller
(74) *Attorney, Agent, or Firm* — Lowe Graham Jones PLLC

(57) ABSTRACT

The present disclosure is directed to methods of making coffee products containing cannabinoids that are extracted from *Cannabis* plant. According to one embodiment, the method includes the steps of (a) extracting cannabinoids from the *Cannabis* plant; and (b) admixing the cannabinoids into a coffee product. The disclosed methods produce coffee products that possess the benefits of both coffee and *Cannabis* plant. The methods can be used to produce different coffee products including single-serve coffee pods, ground coffee, espresso and coffee extracts. The methods are used to make coffee and other products with desired and consistent amount of *Cannabis*-derived compounds.

5 Claims, 2 Drawing Sheets

METHOD FOR MAKING COFFEE PRODUCTS CONTAINING CANNABIS INGREDIENTS

PRIORITY CLAIM

This application is a continuation-in-part of U.S. patent application Ser. No. 15/837,623 filed Dec. 11, 2017; which is a divisional of U.S. patent application Ser. No. 15/397,895 filed Jan. 4, 2017; which is a continuation of U.S. patent application Ser. No. 14/819,830 filed Aug. 6, 2015; which claims priority from U.S. Patent Application No. 62/037,827 filed Aug. 15, 2014, which applications are incorporated herein by reference in their entireties.

FIELD OF THE INVENTION

In light of marijuana legalization in multiple states, adding *Cannabis* derived compounds (CannDC) to various foods and beverages, e.g., coffee drinks, is now feasible.

The invention disclosed and taught herein generally relates to methods for making coffee products containing *Cannabis* derived compounds (CannDC). In particular, methods for admixing coffee and CannDC, e.g., cannabinoids, terpenes, and flavonoids. CannDC can be used to describe single compounds (e.g., THC (a single cannabinoid) or myrcene (a single terpene) or multiple compounds in the same class of compounds (e.g., THC and CBD (cannabinoids) or multiple compounds of different classes of compounds (e.g., THC and CBD (cannabinoids) plus myrcene and pinene (terpenes)).

BACKGROUND OF THE INVENTION

Cannabinoids are compounds that are concentrated in a viscous resin produced in structures known as glandular trichomes of the *Cannabis* plant. At least 113 different cannabinoids have been isolated from the *Cannabis* plant and some of the most well studied cannabinoids are delta-9-tetrahydrocannabinol (THC), tetrahydrocannabinolic acid (THC-A), cannabidiol (CBD), cannabidiolic acid, (CBD-A), and cannabinol (CBN). THC is one of the primary psychoactive CannDC found within the *Cannabis* plant. Terpenes are aromatic compounds found within the *Cannabis* plant and vary with strain, with greater than 100 terpenes identified in the *Cannabis* plant. Terpenes evoke olfactory and gustatory responses in humans, namely odors, tastes, and flavors, and are thought to modulate the effects of cannabinoids. Flavinoids are compounds that give non-green colors to the *Cannabis* plant and also thought to module that effects of the plant.

There are three major species of *Cannabis* recognized, *Cannabis Sativa Cannabis Indica,* and *Cannabis Ruderalis,* with the first two being more widely known. The effects of *Sativa* are anecdotally known to cause a cerebral high, hence it is often used during the day as medical *Cannabis,* while *Indica* is anecdotally known for its sedative effects and thus preferred at nighttime for medical *Cannabis* purposes.

Prior art cannabinoid products include, but are not limited to, U.S. Pat. No. 8,481,091 to Ross, which discloses an aerosol-based cannabinoid and U.S. Pat. No. 6,630,507 to Hampson et al., which teaches the use of cannabinoids as antioxidants and neuroprotectants. Further, published U.S. patent application Pub. No. US 2004/0049059 to Mueller discloses a method for producing a THC and CBD-enriched extract derived from dried *Cannabis* plant material that was extracted using a $CO_2$ extraction method.

THC is the primary psychoactive component of the *Cannabis* plant, and its concentration varies from species to species and strain to strain of the *Cannabis* plant. Further, there are various methods of extracting THC, and other CannDC, from the *Cannabis* plant. However, there currently exist no patented methods to provide coffee beverages infused with CannDC with standardized doses or consistent amounts of CannDC. Thus, there is a need in the art for methods of preparing coffee products with consistent amounts of CannDC.

SUMMARY OF THE INVENTION

The present disclosure is directed to methods of making coffee products containing *Cannabis*-derived compounds, i.e., CannDC, e.g., cannabinoids. This disclosure also includes cannabinoids derived from other plants (e.g., hops and daisy varieties), genetically modified crops that contain metabolically engineered pathways capable of producing cannabinoids, microbes (e.g., yeast) and other organisms; with cannabinoids being defined as any compound that affect or modulate currently known endocannabinoid receptors (CB1, CB2, GPR18, GPR55, GPR119, and TRPV1) or future discovered endocannabinoid receptors, within humans or other living organisms; this includes cannabinoids acting as receptor agonists, partial agonists, antagonists, partial antagonists, or allosteric regulators. The innovative methods disclosed here are to produce coffee products that possess the benefits of both coffee and the *Cannabis* plant. These methods can be used to produce different coffee products, including but not limited to, single serve coffee pods, ground coffee, coffee extract (e.g., instant coffee), and espresso.

The disclosed methods for making coffee products include admixing CannDC into coffee products. In one embodiment, the method includes the steps of (a) extracting CannDC from the *Cannabis* plant; and (b) admixing the cannabinoids into a coffee product.

Various methods for extracting CannDC from the *Cannabis* plant are known in the art. Most methods include using a hydrocarbon solvent, such as ethanol, butane, pentane, hexane, heptane, and isopropyl alcohol with other extraction methods including high mechanical force/pressure and supercritical $CO_2$ fluid. According to one embodiment, the method for extracting the active CannDC (e.g., cannabinoids) from the *Cannabis* plant included the steps of (a) extracting cannabinoids using supercritical $CO_2$ fluid as a solvent; (b) evaporating or purging off the solvent; and (c) heating the cannabinoids enriched extract at elevated temperatures (e.g., decarboxylation of THC-A to THC). According to another embodiment, isopropyl alcohol is used as a substitute for supercritical $CO_2$ fluid. According to yet another embodiment, butane is used as a substitute for isopropyl alcohol.

There are different methods for admixing or infusing the cannabinoids into a coffee product. According to one embodiment, the cannabinoids can be admixed into a coffee product, for example, whole coffee beans or ground coffee beans, after cannabinoids were heated at elevated temperature. According to another preferred embodiment, the cannabinoids are first premixed with propylene glycol at elevated temperature to produce a homogenous mixture; the homogenous mixture is then admixed or infused into a coffee product.

There are different methods for producing a coffee product with consistent amounts of CannDC. According to one embodiment, key cannabinoids in a mixture of CannDC was analyzed by an analytical lab, and the results were used to control how much of the key cannabinoids would be required to provide a consistent amount of CannDC in a coffee product. According to another embodiment, by using the same plant species, and by using supercritical $CO_2$ fluid to extract, the key cannabinoids could be used to generate a consistent amount of one cannabinoid, THC, and consequently, producing a coffee product with consistent amount of THC without analyzing all the batches of cannabinoids.

The claimed method includes a coffee product with CannDC in a single-serve container that can be brewed to provide a consumable coffee product that contains from 1 mg to 100 mg of CannDC, either single compounds (e.g., THC or CBD) or combinations of CannDC (e.g., cannabinoids and terpenes, per serving Further, the claimed method includes a coffee product in a multi-serve container or can be used in a multiple serving coffee brewing unit to provide a consumable coffee drink that contains from 1 mg to 100 mg of THC.

These and other characteristics of the disclosed embodiments will become more apparent from the following description and illustrative embodiments, which are described in detail with reference to the accompanying drawings.

BRIEF DESCRIPTION OF THE DRAWINGS

Preferred and alternative examples of the present invention are described in detail below with reference to the following drawings.

The drawings show a sample embodiment of a single-serve coffee infused with THC in accordance with the present invention, the details of which are explained below. In the drawings.

DETAILED DESCRIPTION OF THE PREFERRED EMBODIMENT

Figure 1:
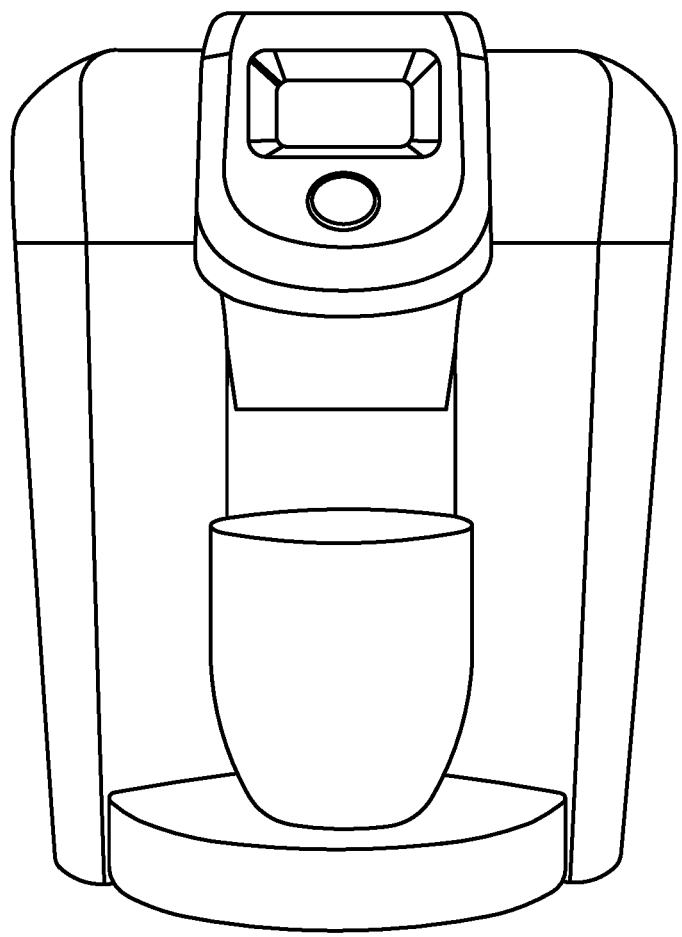
FIG. 1 is an illustration of a prior art brewer designed to brew a cup of coffee with a single-serve unit containing coffee grounds infused with THC enriched resin extracted from the *Cannabis* plant.
Figure 2:
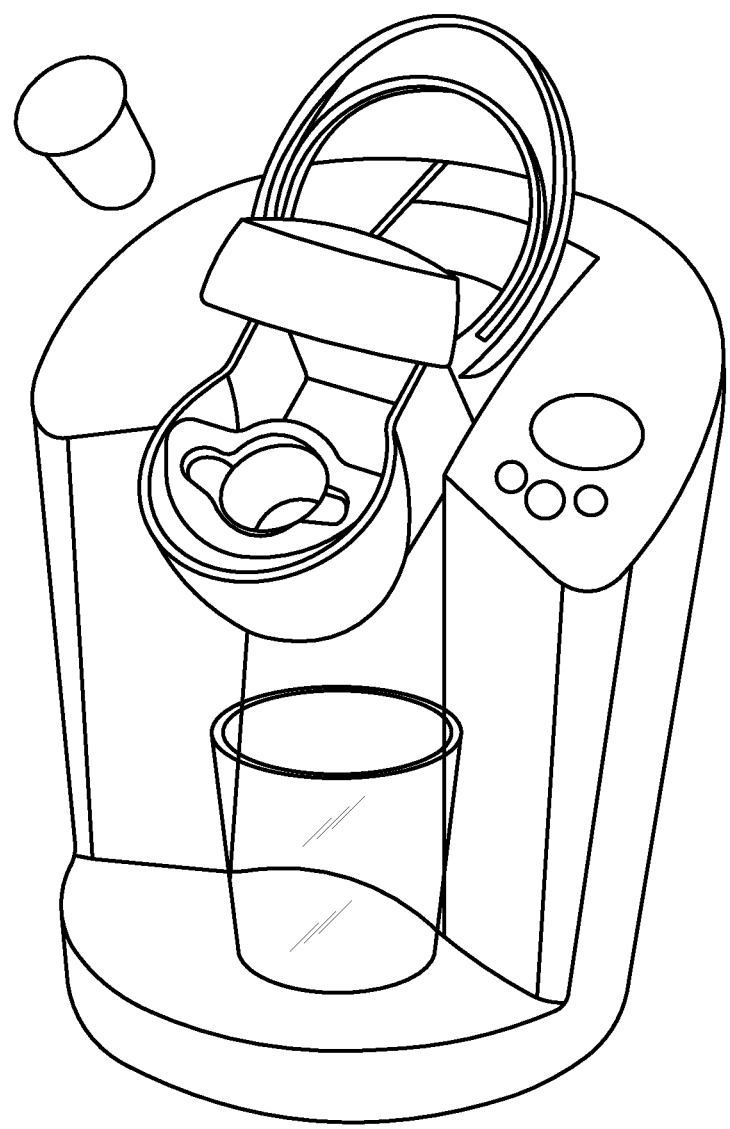
FIG. 2 is an illustration of a prior art brewer designed to brew a cup of coffee with a single-serve unit containing coffee grounds infused with THC enriched resin extracted from the *Cannabis* plant.

The present disclosure is directed to inventive methods of making coffee products containing CannDC. The disclosed method produces a coffee product that possesses the benefits of both coffee and the active ingredients of the *Cannabis* plant. The method can be used to produce different coffee products with a desired and consistent amount of any single CannDC (e.g., THC or CBD) or combinations of CannDC (e.g., cannabinoids and terpenes).

According to one embodiment of the invention, the instantly claimed method can be used to produce a coffee product (with additional flavor if desired) with a consistent and predictable amount of CannDC per serving using a coffee brewer for both home and commercial use. The coffee brewer can be any conventional coffee brewer that makes single or multiple cups of coffee. For example, the coffee product can be obtained by using a K-Cup®, i.e., a single-serving coffee brewing system. Wherein each K-Cup® is a plastic container with a coffee filter inside and ground coffee beans (flavored or unflavored) treated with a specific amount of CannDC packed together in the K-Cup® and sealed air-tight with a combination plastic and foil lid. When the K-Cup® is placed in an accommodating brewer, the brewer punctures both the foil lid and the bottom of the K-Cup® and forces hot water under pressure through the K-Cup® and into a cup to provide a consumable coffee drink containing a specified quantity of active cannabinoid compound (s). Further envisioned is the use of specific amounts of THC (and/or other CannDC) not only for coffee, but K-Cup® varieties including for example, tea, hot chocolate, iced tea, as well as fruit drinks.

The use of a K-Cup® or single-serve unit is not limited to the design of a K-Cup® and includes any single or multi-serve container or packaging which provides for the delivery of THC (and/or other CannDC) with the consumable drink that can be processed by an accommodating brewing or mixing apparatus.

According to a specific embodiment of the invention, the method is directed to making coffee products containing CannDC that are extracted from the *Cannabis* plant using single-use units that contain ground coffee and a specific quantity of CannDC in suspended in a lipophilic solvent (e.g., propylene glycol, vegetable glycerin, medium chained triglycerides, or other oils), which then can be placed in an accommodating coffee brewing apparatus to provide a consumable coffee beverage. The lipophilic solvent is meant to create a partial or full emulsion for homogenizing the CannDC content with the coffee beverage.

The presently claimed process envisions the use of various products, e.g., coffee, tea, hot chocolate and the like that include CannDC in single-use or multi-volume units that can be used with, for example single or multi brewing apparatus, with consumable fluids such as water (hot or cold), juice, milk, etc., to produce the desired consumable beverage.

Various systems for making and delivering individual and customized beverage products for a consumer are known in the art. U.S. Pat. Nos. 6,759,072, 7,438,941, 8,336,186, 8,586,117, and 8,720,320 disclose, inter alia, various liquid infusion and/or brewing processes, as well as various assemblies and containers (e.g., pods) to hold materials used to provide single-serve or multi-serving beverages. The entire contents of the references cited are incorporated herein by reference.

The disclosed method for making a coffee product includes the steps of extracting CannDC from the *Cannabis* plant and admixing the CannDC into a coffee product(s).

There are different methods for extracting cannabinoids from the *Cannabis* plant. Most methods include using a solvent, such as butane, hexane, isopropyl alcohol, ethanol, and supercritical $CO_2$ fluid. Hash oil (also known as wax, nectar, full melt, honey, dabs, or budder) is a resinous matrix of cannabinoids obtained from the *Cannabis* plant by solvent extraction or mechanical means, formed into a hardened or viscous mass. According to an embodiment, the hash oil is made by passing liquid butane through a tube filled with *Cannabis* plant matter. The low temperature of the liquid butane crystallizes the *Cannabis* resins. As the butane passes through the tube the crystallized resins are trapped in the liquid butane. As the mixture of butane and resins exits the tube it is caught in a glass container. Butane is a volatile molecule and boils at $-1°$ C., leaving behind the resins only, which are collected from the glass container. This form is known as BHO or "Butane Hash Oil." After obtaining BHO in this method, BHO producers will then vacuum purge their oil in a vacuum chamber. The primary purpose of this step is to purge the remaining butane from the oil, because butane can have adverse health effects if inhaled. This "purging" process, depending on duration of exposure to vacuum and heat, will give the BHO characteristic textures, such as wax, crumble, shatter and budder. According to another embodiment, the hash oil is extracted using isopropyl alcohol.

According to yet another embodiment, the hash oil is extracted using supercritical $CO_2$ fluid and this method is considered one of the most reliable for extracting predictable yields of CannDC.

After solvent extraction, the hash oil (i.e., extracts) are heated to convert cannabinoids from their acid form into their non-acid forms, i.e., a more biologically active form. This conversion process is called decarboxylation and is usually done through manipulation of temperature and pressure of the sample. This includes, but is not limited to, the decarboxylation of $\Delta 9$-tetrahydrocannabinolic acid-A (THC-A) to THC, cannabidiolic acid (CBD-A) to CBD, or cannabigerolic acid (CBG-A) to CBG. During the decarboxylation step, attempts are made to prevent the oxidation of THC into CBN which will occur due to high amounts heat, light and oxygen exposure. Decarboxylation of cannabinoids from their acids is a function of time and temperature, thus at higher temperatures a shorter period of time will be taken for complete decarboxylation of a given amount of cannabinoids in their acid form. The temperature is generally in the range from 80° C. to 150° C., preferably in the range from 100° C. to 125° C. for a period of 30-60 minutes. According to one embodiment, the hash oil was heated at approximately 120° C. for a period of 30-45 minutes.

There are different methods for admixing the CannDC into a coffee product after decarboxylation. For example, the cannabinoids can be admixed into a coffee product at elevated temperature. Alternatively, the cannabinoids are heated together within a lipophilic solvent to yield a low viscosity mixture, and such mixtures make the admixing easier and more consistently than admixing the viscous cannabinoid-rich resins directly. According to one embodiment, the cannabinoids and lipophilic solvent (e.g., propylene glycol) mixture is tested in a lab, and the amount of THC in a coffee product is controlled by adjusting the volume of the mixture based on the concentration of potency test results. Table 1 provides an example of the potency test results:

TABLE 1

Example of the cannabinoids potency test results
Potency Test Results

| Test | Weight % | Conc | Limit |
| --- | --- | --- | --- |
| CBD-V | <0.01% | <0.10 mg/g | N/A |
| CBD-A | <0.01% | <0.10 mg/g | N/A |
| CBG | 1.37% | 13.72 mg/g | N/A |
| CBD | 0.34% | 3.37 mg/g | N/A |
| THC-V | 0.21% | 2.08 mg/g | N/A |
| CBN | 0.80% | 8.04 mg/g | N/A |
| THC | 73.38% | 733.75 mg/g | N/A |
| CBC | 1.47% | 14.67 mg/g | N/A |
| THC-A | <0.01% | <0.10 mg/g | N/A |
| Max THC | 73.38% | 733.75 mg/g | N/A |
| Max CBD | 0.34% | 3.37 mg/g | N/A |
| Total Active | 77.56% | 775.64 mg/g | N/A |
| Total | 77.56% | 775.64 mg/g | N/A |

A coffee product can also be produced by infusing the CannDC into the product, e.g. coffee beans. Infusing is a process of one component(s) permeating or penetrating into another component(s). Here, the cannabinoids are permeating into the coffee beans.

The Food and Drug Administration (FDA) has classified propylene glycol and medium chained triglycerides as "generally recognized as safe," which means that it is acceptable for use in flavorings, drugs, and cosmetics, and as a direct food additive. Therefore, propylene glycol to the extent necessary to dissolve the extracted cannabinoids can be in a final coffee product. Still, other lipophilic solvents, such as other oils, can be used.

There are different methods in producing a coffee product with consistent amounts of CannDC, e.g., THC. The amount of THC in a coffee product is controlled by the amount of the admixed CannDC and its known THC concentration. One method to obtain THC concentration is testing every batch of cannabinoids in an analytical lab. Alternatively, by using the same plant species, and by using supercritical $CO_2$ fluid to extract, the CannDC can be generated with consistent amount of THC, and consequently, a single lab testing may be sufficient for different batches.

EXAMPLE 1 gram of THC extracted via the supercritical $CO_2$ fluid extraction process from the *Cannabis* plant was mixed with about 3-4 mL lipophilic solvent (an approximate 1:3 ratio).

THC was extracted via the above-described supercritical $CO_2$ fluid extraction process from the *Cannabis* plant; 1 gram of the *Cannabis* plant extract was mixed with about 3-4 mL of lipophilic solvent. 7-10 drops of the extract and lipophilic solvent were mixed with 8-12 gram of coffee grinds and placed in a pod (e.g., K-Cup®) for use within a single serve coffee machine.

Similarly, about 7-12 mL of the *Cannabis* plant extract and lipophilic solvent solvent mixture recited supra was added to about one pound of coffee beans and allowed to stand for 24 hours. The coffee beans were then dried and ground for use in single serve units or large volume coffee brewing units (or commercial brewers). The quantity of THC was laboratory measured to provide uniform doses within the single serve or multi volume coffee brewing devices.

The coffee can be treated with varying flavors, including CannDC. Flavors including exemplary doses of THC:

CannaCafé Standard, known as CannaBliss: Standard *Arabica* coffee infused with *Sativa Cannabis* to provide a cognitive uplifting energetic feel; contains 80-100 mg caffeine and 20-25 mg of THC.

French Vanilla: *Sativa Cannabis* with French Vanilla flavoring added; contains 80-100 mg caffeine and 20-25 mg of THC.

Mocha: *Sativa Cannabis* with Mocha flavoring added; contains 80-100 mg caffeine and 20-25 mg of THC.

Caramel: *Sativa Cannabis* with Caramel flavoring added; contains 80-100 mg caffeine and 20-25 mg of THC.

Raging Bull: Higher caffeine dose of about the equivalent of a bold cup of coffee and espresso to provide a very energetic, uplifting head high, paired with *Sativa Cannabis;* contains 200-225 mg of caffeine and 65-70 mg of THC.

Focus: Highly Caffeinated coffee and *Sativa Cannabis* with a low level of THC; contains 175-220 mg of caffeine and 17-25 mg of THC.

Serenity: Decaffeinated coffee with a strong *Indica* based strain; contains 60-70 mg THC Yin Yang: Caffeinated coffee with a hybrid strain consisting of *Sativa* and *Indica;* contains 100 mg of caffeine and 30 mg of THC Other examples are directed to a formulation for a range of concentration of THC doses in a coffee K-cup as brewed on a Keurig® machine. The range being about 5 mg to ~25-50 mg, and in particular 10 mg concentration of THC per dose in a coffee K-cup. The 50 mg of THC dose was directed to a 'medicinal' K-cup.

Increased solubility of THC in coffee was observed upon formulating a supercritical $CO_2$ fluid extracted THC-enriched oil/resin (or THC isolate) with tapioca maltodextrin (TM).

The 10 mg dose was consistently achieved with 60% recovery from the aqueous phase, with the remainder of THC found to be deposited on the ceramic mug at 20% or not recovered at 20%. The medical preparation was found to have a low yield (~15%) and observed to produce TM chunks upon brewing.

THC is a highly lipophilic molecule with an aqueous solubility of 0.003 mg/mL, which amounts to 0.6 mg THC in a 200 mL cup of coffee (the standard volume of a cup of coffee brewed using a Keurig®). The formulation of THC-enriched oil/resin (or THC isolate) and TM improved solubility limitations and achieved the desired dosage levels of 10 and 50 mg of THC-enriched per cup of Keurig® brewed coffee.

The following factors were evaluated in this study: Solubility; Enhancement Optimum Ratio of THC Oil to TM; Uniformity of Dose; and Scalability.

The sourced raw supercritical $CO_2$ fluid extracted oil/resin potency was measured at 21.1% THC. 39.8 mg of $CO_2$ oil/resin was added to 200 mg TM and blended for roughly five minutes using a mortar and pestle for a 1:5 oil to TM ratio. 120 mg of the resultant mixture was taken and added to the top of 2039.8 mg coffee in a K-Cup. The cup was then sealed and brewed through the provided Keurig® machine. Three separate aliquots were taken from the resultant cup, C1 (top), C2 (middle), C3 (bottom). 0.5 mL from each sample was added to 0.5 mL of methanol and centrifuged to remove solids. 0.5 mL of supernatant was then aliquoted into HPLC vials and assayed by HPLC-UV (high performance liquid chromatography with ultraviolet light detection). The volume of the cup of coffee was measured to be 194 mL.

TABLE 2

Summary of THC Solubility Enhancement.

| Measurement | Top | Middle | Bottom |
|---|---|---|---|
| THC Input | 4.2 mg | 4.2 mg | 4.2 mg |
| THC Recovered | 0.8 mg | 0.8 mg | 0.8 mg |
| Recovery % | 19.1% | 19.1% | 19.1% |

The observed 0.8 mg of THC observed in the THC/TM formulation was not much better than the literature reported value of 0.6 mg of THC.

Due to this, an investigation of the used filter and coffee grounds was conducted. Extraction and subsequent HPLC-UV analysis of the used filter and coffee grounds found a substantial amount of THC being left behind in those materials.

To avoid this loss of THC, the examples were performed by placing the THC/TM formulation beneath the filter in the K-cup.

Batches of supercritical $CO_2$ fluid extracted oil/resin and TM were made using the method described in the 'Solubility' section to achieve ratios of 1:5, 1:10, and 1:15 (THC Oil:TM). Aliquots were taken out of the oil/TM mixes and dissolved separately into 10 mL of water and into 10 mL of coffee and assayed for THC concentration using HPLC-UV.

TABLE 3

Summary of 1:5, 1:10 and 1:15 $CO_2$/TM mixes.

| Measurement | 1:5 water | 1:10 water | 1:15 water | 1:5 coffee | 1:10 coffee | 1:15 coffee |
|---|---|---|---|---|---|---|
| THC Concentration (mg/mL) | 0.060 | 0.048 | 0.067 | 0.160 | 0.563 | 0.578 |
| Theoretical mg of THC in 200 mL cup of coffee | 12.0 | 9.6 | 13.3 | 32.0 | 112.6 | 115.1 |

The 1:10 $CO_2$ oil/TM mix was deemed the best mix to use due a lack of increase in solubility being observed by increasing the TM ratio above 1:10.

The solubility of the THC/TM formulation was much higher in the coffee samples than in the water samples. This suggests that there are components within the coffee solution, which significantly impact the solubility of the formulation.

This example investigated how THC was interacting with the coffee mug after it had been brewed. A cup of coffee was brewed with the 1:10 oil/TM mix placed in the K-Cup underneath the filter containing coffee grounds.

Two separate aliquots were taken from the cup (top and middle), and then coffee was carefully poured out. Methanol was added to the cup and the oil that had condensed to the sides of the cup was dissolved and quantified.

The sample taken from the top of the coffee cup was more concentrated in THC than a sample taken from the middle of the cup. This is consistent with the notion that the lipophilic THC molecule should selectively occupy an oily top layer of a cup of coffee.

TABLE 4

Summary of Coffee Mug Cross Section Analysis.
Total THC input was 11.4 mg.

| Measurement | Top * | Middle * | Cup | Coffee Grounds and Filter | Unrecovered ** |
|---|---|---|---|---|---|
| THC recovered | 7.4 mg | 6.4 mg | 2.4 mg | <0.1 mg | 2.2 mg |
| Recovery % | 64.9% | 56.2% | 21.1% | <0.1% | 19.3% |

* Recovery from Top and Middle of cup was extrapolated to a measurement of the full cup of coffee.
** Unrecovered calculation was based on an average of the Top and Middle recoveries.

Overall, the vast majority of THC is making its way out of the K-cup and into the coffee mug. About 20% of the THC is binding to the sides of the ceramic coffee mug. About 20-25% of the THC is found in the oily coffee film at the top of the cup of coffee.

Under these conditions approximately 60% of the THC would be in the coffee, 20% would remain in the cup after drinking, and 20% is lost (unknown cause, most likely in the oily film floating at the top of the coffee, either consumed or not depending on user). Potential other pathways for loss would be determined in future experiments (chemical modification, volatilization, etc.).

To measure scalability, one 1:10 THC/TM mix was prepared as described above and its contents were analyzed in full. A four times larger preparation of 1:10 THC/TM mix was also prepared, and then divided into four different K-Cups to be processed and analyzed. The data obtained is presented below in Table 5.

TABLE 5

Assessment of the scalability of 1:10 THC/TM mix.

| Measurement | QC Cup | #2 | #3 | #4 | #5 |
|---|---|---|---|---|---|
| THC Input | 17.9 mg | 12.1 mg | 12.3 mg | 12.2 mg | 12.3 mg |
| THC Recovered | 7 mg | 6.8 mg | 7.2 mg | 7.0 mg | 7.6 mg |
| Recovery % | 39.1% | 56.2% | 58.5% | 57.4% | 61.8% |

The preparation scale-up did not negatively affect the THC recovery from coffee. To the contrary a small increase in recovery was observed in the larger scale preparation samples.

The relatively small relative standard deviation (RSD=4.8%) suggests that the K-cups can be expected to reliably produce a consistent dose of THC.

Additionally, a cup of coffee was brewed immediately after a THC-cup and did not contain any detectable amount of THC.

The description has not attempted to exhaustively enumerate all possible variations. That alternate embodiments may not have been presented for a specific portion of the invention, and may result from a different combination of described portions, or that other non-described alternate embodiments may be available for a portion, is not to be considered a disclaimer of those alternate embodiments. It will be appreciated that many of those non-described embodiments are within the literal scope of the following claims, and others are equivalent.

While the preferred embodiment of the invention has been illustrated and described, as noted above, many changes can be made without departing from the spirit and scope of the invention. Accordingly, the scope of the invention is not limited by the disclosure of the preferred embodiment. Instead, the invention should be determined entirely by reference to the claims that follow.

The embodiments of the invention in which an exclusive property or privilege is claimed are defined as follows:

1. A method of making a coffee product consisting essentially of:
    obtaining a cannabis extract from cannabis using a solvent selected from the group consisting of butane, isopropyl alcohol and liquid carbon dioxide to yield the cannabis extract; and
    combining the cannabis extract with coffee, maltodextrin and propylene glycol to yield the coffee product.

2. The method according to claim 1, wherein the obtaining step further evaporates the solvent.

3. The method according to claim 1, wherein the obtaining is performed at an elevated temperature relative to the cannabis.

4. The method according to claim 1, wherein the combining admixes the cannabis extract, maltodextrin and propylene glycol with the coffee.

5. The method according to claim 1, wherein the combining infuses the cannabis extract, maltodextrin and propylene glycol into the coffee.

\* \* \* \* \*